United States Patent
Geist et al.

(10) Patent No.: US 12,290,288 B2
(45) Date of Patent: May 6, 2025

(54) SURGICAL DEVICE FOR INSERTION OF GUIDE WIRE AND PEDICLE SCREW

(71) Applicant: Integrity Implants Inc., Palm Beach Gardens, FL (US)

(72) Inventors: Wyatt Drake Geist, Davie, FL (US); Steven Vanni, North Miami, FL (US)

(73) Assignee: Integrity Implants Inc., Palm Beach Gardens, FL (US)

(*) Notice: Subject to any disclaimer, the term of this patent is extended or adjusted under 35 U.S.C. 154(b) by 258 days.

(21) Appl. No.: 17/938,722

(22) Filed: Oct. 7, 2022

(65) Prior Publication Data
US 2023/0110238 A1   Apr. 13, 2023

Related U.S. Application Data

(62) Division of application No. 16/723,221, filed on Dec. 20, 2019, now Pat. No. 11,484,351.

(60) Provisional application No. 62/783,007, filed on Dec. 20, 2018.

(51) Int. Cl.
*A61B 17/70* (2006.01)
*A61B 17/88* (2006.01)
*A61B 17/90* (2006.01)

(52) U.S. Cl.
CPC ...... *A61B 17/7082* (2013.01); *A61B 17/8875* (2013.01); *A61B 17/8897* (2013.01); *A61B 17/90* (2021.08)

(58) Field of Classification Search
CPC .............. A61B 17/7082; A61B 17/8897
See application file for complete search history.

(56) References Cited

U.S. PATENT DOCUMENTS

| | | | | |
|---|---|---|---|---|
| 2,243,717 A | * | 5/1941 | Moreira | A61B 17/742 411/548 |
| 4,341,206 A | * | 7/1982 | Perrett | A61B 17/746 606/97 |
| 5,632,745 A | * | 5/1997 | Schwartz | A61L 27/58 606/77 |
| 6,436,100 B1 | * | 8/2002 | Berger | A61B 17/864 411/394 |

(Continued)

OTHER PUBLICATIONS

Anonymous, Astura Spine, Retrieved from Internet Mar. 19, 2020, https://asturamedical.com/product/olympic-mis/.

(Continued)

*Primary Examiner* — Christian A Sevilla
(74) *Attorney, Agent, or Firm* — McHale & Slavin, P.A.

(57) ABSTRACT

The invention relates to a surgical tool and method for forming a pilot bore by inserting a guide wire into bone. The surgical tool is also constructed to insert a bone screw that is preloaded onto the surgical tool with a guide wire extending along the longitudinal axis of the bone screw. This construction allows the guide wire and the bone screw to be located and placed without removing the tool from the surgical site. More particularly, the device includes a cannulated hand grip and driving tool used for the rotation of a pedicle screw into bone. The rear portion of the hand grip includes a slide assembly that is suited to grip a guide wire. The slide assembly includes a T-handle to control the sliding movement of the guide wire. The rear surface of the slide is constructed to be impacted with a hammer or similar device.

14 Claims, 5 Drawing Sheets

(56) References Cited

U.S. PATENT DOCUMENTS

| | | | | |
|---|---|---|---|---|
| 7,914,539 | B2* | 3/2011 | Stone | A61B 17/0642 |
| | | | | 606/76 |
| 9,060,748 | B2* | 6/2015 | Housman | A61B 17/8875 |
| 2011/0054537 | A1 | 3/2011 | Miller et al. | |
| 2011/0060373 | A1* | 3/2011 | Russell | A61B 17/0401 |
| | | | | 606/86 R |
| 2012/0004665 | A1 | 1/2012 | Defossez et al. | |
| 2014/0094822 | A1 | 4/2014 | Baynham | |
| 2015/0257807 | A1* | 9/2015 | Strnad | A61B 17/8888 |
| | | | | 81/451 |
| 2020/0323566 | A1 | 10/2020 | Geist et al. | |

OTHER PUBLICATIONS

Anonymous, Alfa Tech, Retrieved from Internet Mar. 19, 2020, https://linkedin.com/posts/alfatec-spine_atec-organic-innovation-machine-activity-6628772455886528512-gm5n/.

Anonymous, Dupuy Spine, Retrieved from Internet Mar. 19, 2020, https://vimeo.com/260201759/.

* cited by examiner

SURGICAL DEVICE FOR INSERTION OF GUIDE WIRE AND PEDICLE SCREW

RELATED APPLICATIONS

In accordance with 37 C.F.R. 1.76, a claim of priority is included in an Application Data Sheet filed concurrently herewith. Accordingly, the present invention claims priority as a divisional of U.S. patent application Ser. No. 16/723,221, entitled "SURGICAL DEVICE FOR INSERTION OF GUIDE WIRE AND PEDICLE SCREW", filed on Dec. 20, 2019, which claims priority to U.S. Provisional Patent Application No. 62/783,007, entitled "SURGICAL DEVICE FOR INSERTION OF GUIDE WIRE AND PEDICLE SCREW", filed on Dec. 20, 2018. The contents of the above application are incorporated herein by reference.

FIELD OF THE INVENTION

The invention relates to a surgical device for insertion of a guide wire and a pedicle screw for surgical spinal procedures. In particular, the device includes a driving tool for inserting and positioning a guide wire into bone, in addition to a pedicle screw into a vertebra without removing the device from the surgical site.

BACKGROUND

Medical procedures involving the vertebrae are normally complicated because of the preciseness and accuracy required to avoid both neural damage and injury to major blood vessels. Precision depth guided instruments are required to perform percutaneous spinal surgery. These surgeries sometimes require penetration of the hard cortical bone of the vertebra and traversal of the softer cancellous bone lying thereunder. A large force is normally required by the surgeon to penetrate the cortical bone. Once the cortical bone is penetrated, extreme care must then be taken to avoid rapidly penetrating through all of the cancellous bone. There is also the danger of rapidly passing through the cancellous bone and then through the cortical bone on the other side of the vertebra. This can result in injury or damage to the spinal cord and/or other organs or blood vessels located adjacent the spine. In some instances, the force required to penetrate the cortical bone is greater than a surgeon can apply by hand. In these instances, a hammer or other similar instrument is required to force the instrument through the cortical bone. When a hammer or similar instrument is used, there is a greater danger of the instrument passing rapidly through the cancellous bone and out the other side of the vertebra.

Thus, what is needed is a device and method for inserting a small diameter guide wire that provides the surgeon with a handgrip to control the depth the wire penetrates. The device and method should also be constructed to allow the user to place a pedicle screw in the bone without removing the tool from the surgical site.

SUMMARY

Briefly, the invention relates to a surgical tool and method for forming a pilot bore by inserting a guide wire into bone. The surgical tool is also constructed to insert a bone screw that is preloaded onto the surgical tool with a guide wire extending along the longitudinal axis of the bone screw. This construction allows the guide wire and the bone screw to be located and placed without removing the tool from the surgical site. The surgical tool is constructed and arranged for use in conjunction with X-ray or ultrasound machines. More particularly, the device includes a cannulated hand grip and driving tool used for the rotation of a pedicle screw into bone. The rear portion of the hand grip includes a slide assembly that is suited to grip a guide wire. The slide assembly includes a T-handle to control the sliding movement of the guide wire. The rear surface of the slide is constructed to be impacted with a hammer or similar device. Should it be desired that the wire be retracted, the T-handle is included to allow the wire to be retracted by hand. The hand grip is securable to various surgical driving tools for the purpose of providing the ability to cooperate with various brands of pedicle screws and other surgical implants for spinal procedures. Thus, more than one driving tool may be secured to the same surgical tool, and the driving tool is rotatable about the longitudinal axis of the surgical tool. This construction saves the surgeon time by forming the pilot bore which may retain the guide wire. Since the pedicle screw is already positioned on the guide wire, the surgeon need only rotate the tool to insert the screw along the guide wire to its desired position. Once the screw is placed, the T-handle can be utilized to retract the guide wire.

Accordingly, it is an objective of the present invention to provide a surgical tool which can be utilized to provide a precise trajectory and insertion of a guide wire along with a bone screw without removal of the tool from the surgical site.

It is another objective of the present invention to provide a surgical tool for insertion of guide wires which can be secured to various drive tools for the insertion of a pedicle screw into a patient.

It is yet another objective of the present invention to provide a surgical tool for the insertion of a guide wire that includes a T-handle for retracting or removing a guide wire.

Still yet another objective of the present invention is to provide a surgical tool for formation of a pilot bore by insertion of a guide wire that includes a driving surface for a striking instrument.

Still yet a further objective of the present invention is to provide a surgical tool that can be used to ensure a desired trajectory and/or depth of a pilot hole by advancing a guide wire for placement of spinal implants, including ensuring proper placement of pedicle screws during pedicle fixation procedures and ensuring proper trajectory during the establishment of an operative corridor to a target site.

Other objects and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DETAILED DESCRIPTION

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Various embodiments and surgical uses of devices are described for enhancing the safety and efficiency of surgical procedures. In one example, set forth by way of example only, the present invention may facilitate safe and reproducible pedicle screw guidance and placement by controlling the axial trajectory of a guide wire for pilot hole formation and/or screw insertion. In another example, set forth by way of example only, intraoperative imaging performance may be improved and radiation exposure minimized by providing control to the surgeon during guide wire depth placement. In yet another example, controlling the trajectory and depth of surgical access instruments can aid in both the insertion and positioning of the access instruments themselves, as well as aiding in the later insertion of instruments and/or implants through or with the surgical access instruments. It is expressly noted that these examples are set forth by way of example, and that the present invention may be suitable for use in any number of additional surgical actions where the angular orientation, trajectory or depth (linear distance traveled) of instrumentation and/or implants is important.

Figure 1:
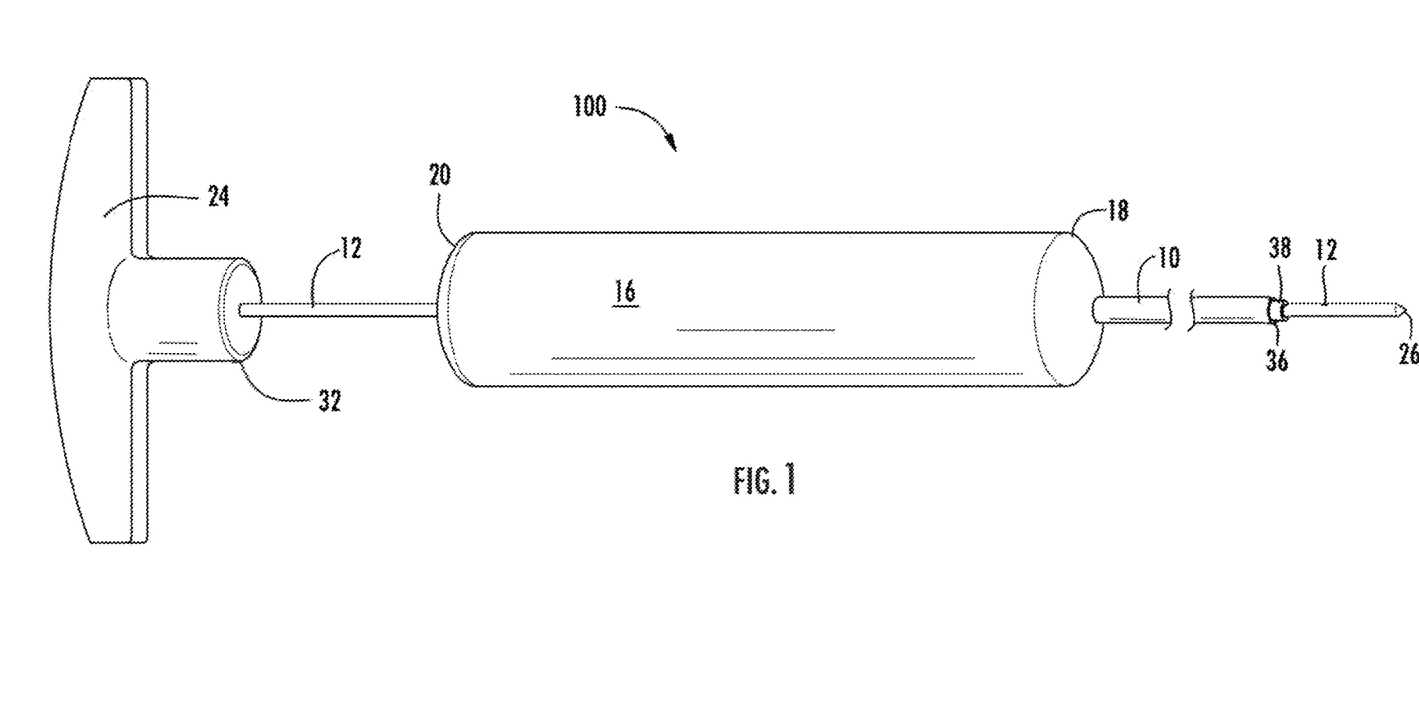
FIG. 1 is a front perspective view of one embodiment of the surgical tool, illustrated with a guide wire and a driving tool for a pedicle screw.
Figure 2:
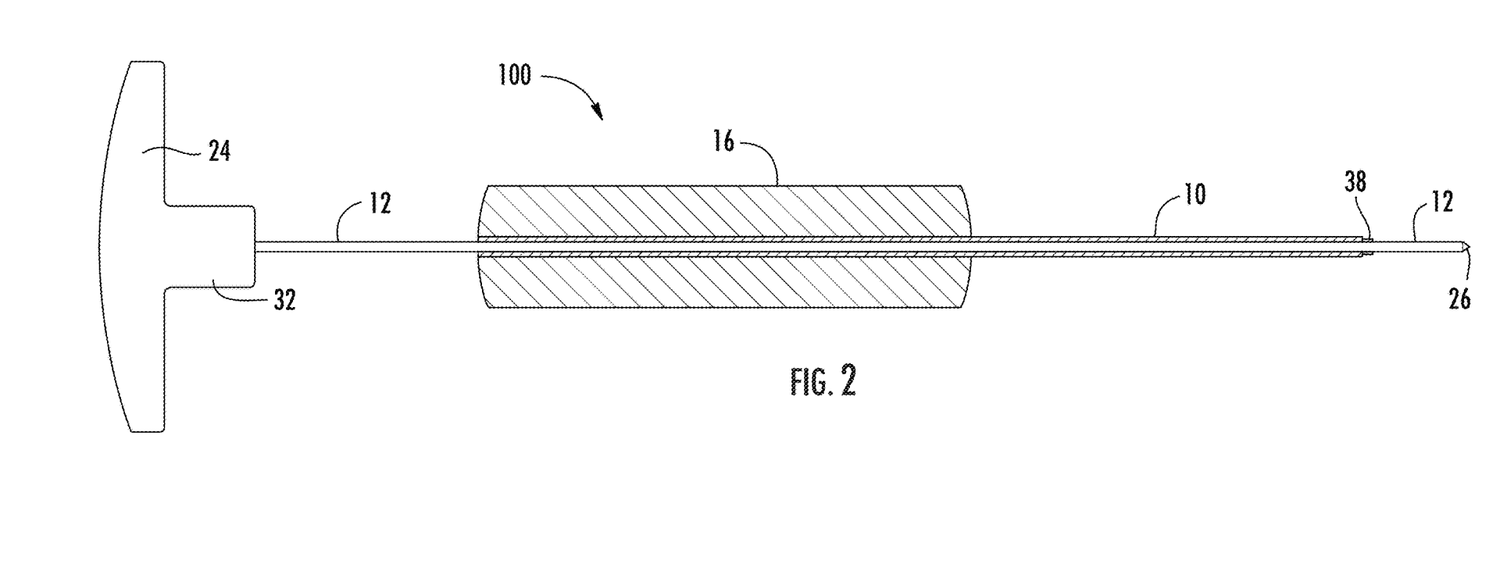
FIG. 2 is a side view, partially in section, illustrating the embodiment shown in FIG. 1.
Figure 3:
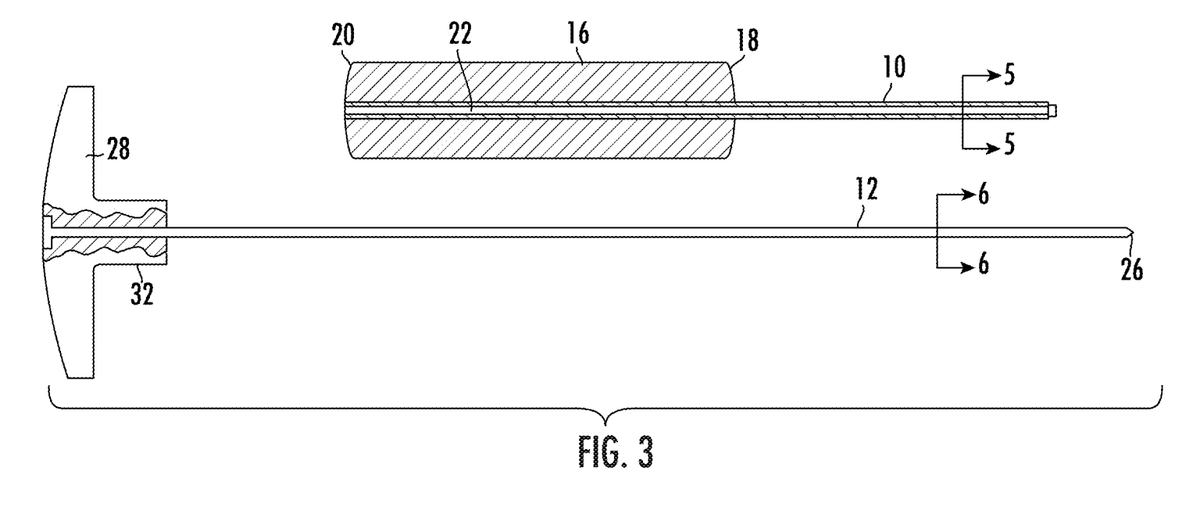
FIG. 3 is an exploded side view of the embodiment shown in FIG. 2, illustrated partially in section.
Figure 4:
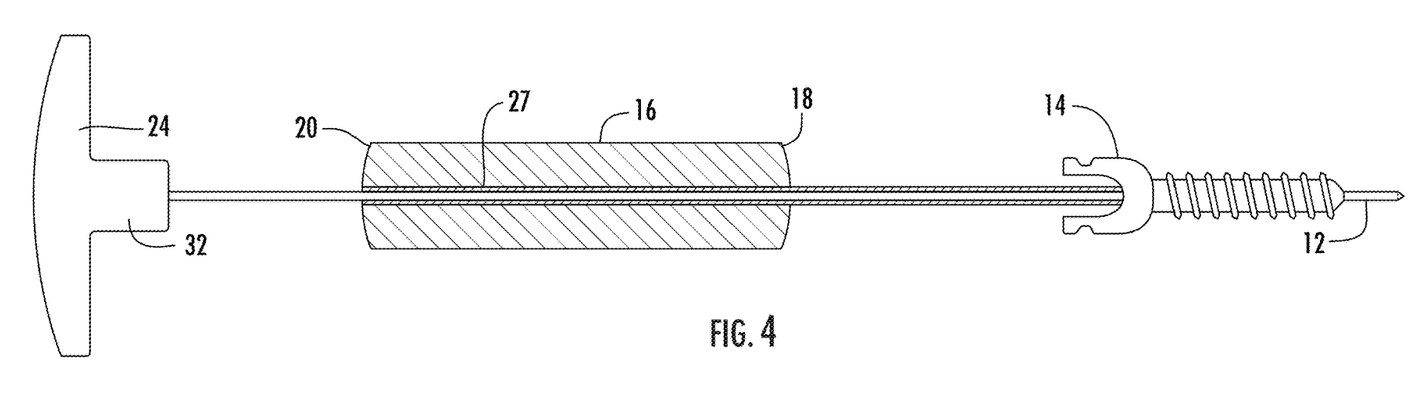
FIG. 4 is side view illustrating the surgical tool in combination with a pedicle screw.
Figure 5A:
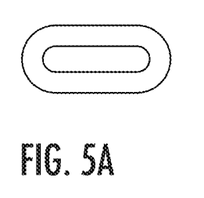
FIG. 5A is a cross-sectional view of one embodiment of the driving tool taken along lines 5-5 of FIG. 3.
Figure 5B:
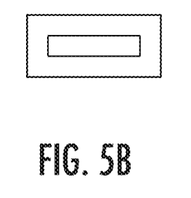
FIG. 5B is a cross-sectional view of one embodiment of the driving tool taken along lines 5-5 of FIG. 3.
Figure 6A:
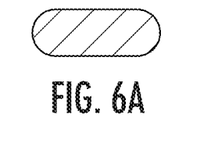
FIG. 6A is a cross-sectional view of one embodiment of the guide wire taken along lines 6-6 of FIG. 3.
Figure 6B:
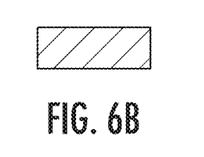
FIG. 6B is a cross-sectional view of one embodiment of the guide wire taken along lines 6-6 of FIG. 3.

FIGS. 1-6B, which are now referenced, illustrate one embodiment of the present invention and one manner in which it may be assembled. Like reference numerals refer to like components in the various figures. FIGS. 1-6B illustrate a surgical tool 100 for operation of a driving tool 10, a guide wire 12 and a bone screw 14. By way of example only, while placing bone screws through a pedicle (which is a small generally tubular structure connecting posterior elements of a vertebra to the vertebral body), it is critical to ensure the bone screw is contained within the pedicle and does not breach the outer pedicle wall. Since the pedicle is surrounded by delicate nerve tissue, a breach can have serious consequences for the patient, ranging from mild pain to paralysis. One way to mitigate the risk of a pedicle breach during screw placement (including preparation for screw placement, such as pilot hole formation and tapping) is to determine the angular orientation of the pedicle, and thereafter advance the necessary instruments, guide wires and screws along the determined trajectory. By orienting the surgical access components along the pedicle trajectory with a guide wire, the surgical instruments and pedicle screws may be simply and efficiently advanced along the same trajectory, and thus avoid a breach.

Thus, in spinal surgery, before the pilot hole is formed with the guide wire 12, the desired angular trajectory must first be determined. Preoperative superior view utilizing AP fluoroscopy, MRI or CAT scan imaging device(s) are used to determine the trajectory once the surgical tool 100, in combination with the driving tool 10, pedicle screw 14, and guide wire 12, has been placed at the anatomical site for which the surgery is to be conducted. C-arm fluoroscopes are used extensively during many surgical procedures. During spinal surgery, for example, the C-arm is used frequently to help locate specific structures of the spine, to direct the positioning of surgical instruments and/or instrumentation, and to verify the proper alignment and height of vertebra, among other uses. Imaging devices, such as the C-arm, are typically provided with a scale (not shown) indicating the orientation of the radiography beam with respect to the patient, and thus, in this example, the surgical tool 100 in combination with the driving tool 10, pedicle screw 14 and guide wire 12.

FIGS. 1-6B, which are now referenced, illustrate one embodiment of the present invention and the manner in which it is constructed. In general, the figures illustrate a surgical tool 100 for creating a precise pilot bore using a guide wire 12 in a bone structure. The surgical tool 100 can further insert a bone screw 14 into the pilot bore without removal of the tool from the surgical site. The surgical tool 100 comprises a substantially rigid cannulated hand grip 16 including a first end 18 and a second end 20, the first end 18 including a cannulated driving tool 10, the second end 20 including a cannula 27 for housing a T-handle slide 24. The hand grip 16 is secured to the cannula 27 in a manner that prevents rotation between the two. The hand grip 16 may be fixed to the cannula 27 by various means, which include overmolding, or can be detachably removable. In embodiments where the hand grip 16 is detachably removable, the hand grip may include adhesive, keyways, press fits, serrations or the like, which allow the hand grip to adhere to the cannula 27 to prevent rotation between the hand grip 16 and the cannula 27 during operation. The overmolding or other fixation between the cannula 27 and the hand grip 16 prevent it from pulling out of the surgical tool 100, while allowing the surgical tool 100 to rotate the driving tool 10 in either direction. The distal end 36 of the driving tool 10 includes a shaped driver 38 which is constructed to cooperate with a female cavity in a bone screw 14 to allow the screw to be rotated into or out of a bone. The driving tool 10 includes a bore extending along the longitudinal axis of the driving tool 10 for passage of a guide wire 12. The construction of the hand grip 16 allows the hand grip 16 and driving tool 10 to be changed to exchange the shaped driver 38 for different shapes which apply to different brands of surgical screws.

Still referring to FIGS. 1-6B, the cannula 27 and driving tool 10 are generally tubular members having the cannulated shaped driver 38 positioned on a distal end 36 of the driving tool 10. The cannula bore 22 is sized to allow the guide wire 12 to travel through the hand grip 16, cannula 27, and driving tool 10. In at least one embodiment, the guide wire 12, cannula 27, and driving tool 10 may include shapes that cooperate with each other to prevent rotation of the guide wire 12 within the surgical tool 100. Such shapes may include polygons and ovals that are relatively easy to form and prevent any unwanted rotation between the components of the surgical tool 100.

Still referring to FIGS. 1-6B, the T-handle slide 24 is generally constructed and arranged to allow the surgeon to control the travel of the guide wire 12 within the surgical tool assembly 100. The T-handle slide 24 includes a T-handle head 28 and guide wire 12. The guide wire 12 includes distal end 26 which may be pointed, have a trocar point, or any other suitable end for piercing bone. The T-handle head 28 is constructed to cooperate with the guide wire 12 to allow the guide wire 12 to be malleted into a desired position, as well as retracted by pulling or prying against the T-handle, without separation from the guide wire 12. The T-handle head 28 includes a stop portion 32, which extends from the T-handle head 28. The stop portion 32 stops the traversal of the guide wire 12 through the surgical tool 100 once the stop portion 32 contacts the second end 20 of the hand grip 16. The stop portion 32 also provides an area of increased thickness to the T-handle slide 24, which allows the guide wire 12 to be secured sufficiently to the T-handle head 28 by overmolding or the like. In this manner, the T-handle slide 24 can be economically manufactured to stand up to being malleted or pulled to prevent separation of the two components. In the preferred embodiment, the hand grip 16 is constructed from a material such as plastic, while the cannula 27 and driving tool 10 are constructed from a suitable metal such as stainless steel. Likewise, the T-handle head 28 is also preferable constructed from a material such as plastic, while the guide wire 12 is constructed from a suitable metal such as stainless steel or nitinol.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention, and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A surgical tool for insertion of a guide wire and a bone screw comprising:
    a surgical tool including a hand grip, said surgical tool including a first end and a second end, said first end including a cannulated driving tool, said second end including said hand grip comprising a first hand grip portion, said hand grip being cannulated such that said hand grip cannula and said driving tool cannula are aligned along a longitudinal axis of said surgical tool forming a guide path, a slide assembly having a second hand grip portion and an elongated guide wire extending outwardly from said second hand grip portion, said guide wire sized to extend through said cannula and having a length sufficient to extend through said guide path to protrude from said first end of said driving tool, a distal end of said driving tool including a shaped driver which is constructed to cooperate with a bone screw to allow said bone screw to be rotated into or out of a bone with manual rotation of said hand grip, said shaped driver constructed and arranged to be locked to said bone screw so that said bone screw is axially aligned with said longitudinal axis, said bone screw including a cannula extending along the longitudinal axis of said bone screw, wherein said guide wire is configured to be positioned to extend through said surgical tool and said bone screw, said guide wire having a sharp tip allowing said surgical tool, when assembled with said bone screw and said guide wire, to be inserted through the skin of a patient in-vivo to position said sharp tip adjacent a bone, said surgical tool utilized to provide a trajectory for said guide wire and said bone screw for insertion of said bone screw into a bone;
    wherein the guide wire includes a non-round shape and said guide path includes an inner shape constructed and arranged to cooperate with the non-round shape of the guide wire to allow rotation of said guide wire together with said surgical tool such that rotation of the hand grip results in rotation of the guide wire.

2. The surgical tool of claim 1 wherein said second hand grip portion is constructed to cooperate with said guide wire to allow said guide wire to be malleted into a desired position within said bone.

3. The surgical tool of claim 2 wherein said second hand grip portion includes a stop portion, said stop portion constructed and arranged for stopping the traversal of said guide wire through said surgical tool, thereby limiting a depth said guide wire can be inserted into said bone.

4. The surgical tool of claim 1 wherein said guide wire is overmolded to form said second hand grip portion, to create a secure permanent connection between the second hand grip portion and the guide wire.

5. The surgical tool of claim 1 wherein said second hand grip portion is constructed to cooperate with said guide wire to allow said guide wire to be retracted from a position within said bone by pulling against said second hand grip portion without separating said hand grip portion from said guide wire.

6. The surgical tool of claim 1 wherein said guide wire is constructed from metal.

7. The surgical tool of claim 1 wherein said second hand grip portion is removably secured to said guide wire, whereby said guide wire can be inserted into a bone, such that said hand grip can be removed from said guide wire without removal of said guide wire from said bone.

8. The surgical tool of claim 7 wherein said second hand grip portion is resecurable to said guide wire.

9. The surgical tool of claim 2 wherein said guide wire includes an enlarged head for securement to said second hand grip portion to allow said guide wire to be driven into a bone or pulled outwardly from a bone without unwanted detachment.

10. The surgical tool of claim 1 wherein said cannula includes a non-round inner bore, said non-round inner bore constructed and arranged to cooperate with a non-round guide wire to prevent rotation of said guide wire within said cannula.

11. The surgical tool of claim 1 wherein the guide path comprises a non-round inner bore and said non-round inner bore of said guide path is a polygon.

12. The surgical tool of claim 1 wherein the guide path comprises a non-round inner bore and said non-round inner bore of said guide path is an oval.

13. The surgical tool of claim 1 wherein said hand grip is secured to said cannulated driving tool in a manner that prevents rotation between said cannulated driving tool and said hand grip.

14. The surgical tool of claim 1 wherein said hand grip is removably secured to said cannulated driving tool in a manner that prevents rotation between said cannulated driving tool and said hand grip.

* * * * *